(12) United States Patent
Tsuie

(10) Patent No.: US 6,440,889 B1
(45) Date of Patent: Aug. 27, 2002

(54) AMINE ELIMINATION PROCESS FOR MAKING SINGLE-SITE CATALYSTS

(75) Inventor: Barbara M. Tsuie, West Chester, OH (US)

(73) Assignee: Equistar Chemicals, LP, Houston, TX (US)

( * ) Notice: Subject to any disclaimer, the term of this patent is extended or adjusted under 35 U.S.C. 154(b) by 24 days.

(21) Appl. No.: 09/930,631

(22) Filed: Aug. 15, 2001

(51) Int. Cl.$^7$ .................. B01J 31/00; C07D 207/00; C07D 209/80

(52) U.S. Cl. .................. 502/152; 548/402; 548/420

(58) Field of Search .................. 502/152; 548/402, 548/420

(56) References Cited

U.S. PATENT DOCUMENTS 6,232,260 B1 * 5/2001 Nagy et al. .................. 502/155

* cited by examiner

Primary Examiner—Taofiq Solola
Assistant Examiner—Joseph Murray
(74) Attorney, Agent, or Firm—Jonathan L. Schuchardt

(57) ABSTRACT

An amine-elimination process for making single-site catalysts is disclosed. First, an indenoindole or its synthetic equivalent reacts with a tetrakis(dialkylamino) Group 4 metal compound to give a tris(dialkyl-amino) compound. This versatile intermediate can be halogenated, alkylated, or reacted directly with cyclopentadienyl precursors to provide valuable indenoindolyl-Group 4 metal complexes. The process selectively provides mono-indenoindolyl complexes. In addition, it enables the economical preparation of desirable Cp- or Cp-like derivatives and allows the use of an inexpensive Group 4 transition metal source.

6 Claims, No Drawings

AMINE ELIMINATION PROCESS FOR MAKING SINGLE-SITE CATALYSTS

FIELD OF THE INVENTION

The invention relates to a process for making olefin polymerization catalysts. In particular, the invention relates to a process for making Group 4 transition metal complexes that incorporate a single anionic indenoindolyl ligand.

BACKGROUND OF THE INVENTION

"Single-site" catalysts, which include metallocenes, actively polymerize olefins to give polymers with valuable properties such as narrow molecular weight distribution and uniform comonomer distribution. While traditional metallocenes have cyclopentadienyl (Cp) ligands and/or Cp-like ligands (e.g., indenyl, fluorenyl), a variety of non-metallocene, single-site catalysts having heteroatomic ring ligands havezalso been developed (see, e.g., U.S. Pat. Nos. 5,554,775 and 5,539,124).

In a series of articles, Professor Richard Jordan and coworkers at the University of Iowa describe the preparation of bridged metallocene complexes via an amine elimination approach (see *Organometallics* 14 (1995) 5; *Organometallics* 15 (1996) 4030, 4038, 4045; and *J. Am. Chem. Soc.* 118 (1996) 8024). In a typical example, 1,2-bis(3-indenyl)ethane reacts with tetrakis(dimethylamino)zirconium ($Zr(NMe_2)_4$) with elimination of two moles of dimethylamine to give bridged bis(dimethylamino)zirconium complexes (see Scheme 1 of the *J. Am. Chem. Soc.* article). Later in the same paper, halogenation or alkylation of the bis(dimethylamino) complex is described (Scheme 3). All of the complexes are bridged metallocenes.

U.S. Pat. No. 6,232,260 discloses single-site catalysts based on organometallic complexes that incorporate at least one indenoindolyl ligand. A typical indenoindolyl precursor is easily made by reacting 1-indanone with p-tolylhydrazine. Examples A and B in the '260 patent illustrate the preparation of a bis(indenoindolyl)zirconium dichloride complex from the reaction of two equivalents of an indenoindolyl monoanion and one equivalent of zirconium tetrachloride. Only bis(indenoindolyl)zirconium complexes are prepared.

PCT Int. Appl. WO 99/24446 describes many indenoindolyl complexes, including bridged complexes, bis(indenoindolyl) complexes, and non-bridged indenoindolyl (Cp) or indenoindolyl(Cp-like) complexes. All of the working examples show either bis(indenoindolyl) complexes or bridged complexes. Based on the reference teachings, which include a listing of many non-bridged indenoindolyl(Cp or Cp-like) complexes, one expects preparation of the latter complexes to be straightforward.

Recently, we became interested in finding a better way to make non-bridged Group 4 organometallic complexes that incorporate one indenoindolyl ligand and one Cp or Cp-like ligand. While these complexes can be made by reacting cyclopentadienylzirconium trichloride with one equivalent of an indenoindolyl monoanion, $CpZrCl_3$ is expensive. Moreover, Cp-like analogs of the starting material are not commercially available.

A logical approach would be to react inexpensive $ZrCl_4$ with one equivalent of an indenoindolyl monoanion, and then react the trichloride product with an anion from cyclopentadiene, indene, or fluorene:

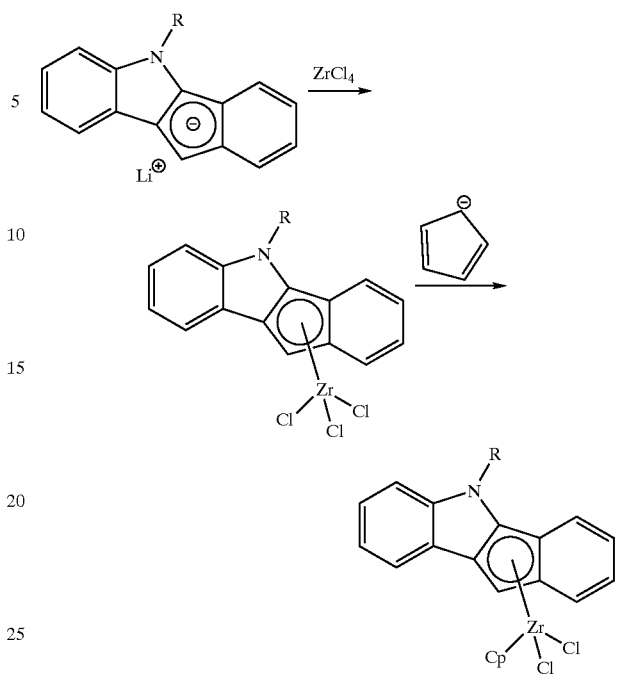

This approach would provide flexibility in the choice of Cp or Cp-like ligand. Unfortunately, however, the initial reaction fails to provide indenoindolylzirconium trichloride selectively. In fact, as our experiments demonstrate, the trichloride product reacts so rapidly with more monoanion that the only isolated product is a bis(indenoindolyl) zirconium dichloride (see Comparative Example 7 below). This problem is not described in either U.S. Pat. No. 6,232,260 or PCT Int. Appl. WO 99/24446.

A valuable process would selectively give non-bridged Group 4 metal indenoindolyl complexes containing little or no bis(indenoindolyl) complex. Preferably, the route would permit flexibility in the choice of Cp or Cp-like ligand while avoiding costly starting materials. Ideally, the process would utilize versatile intermediates that provide pathways to other valuable indenoindolyl Group 4 metal complexes.

SUMMARY OF THE INVENTION

The invention is an improved process, based on amine elimination, for selectively making Group 4 metal complexes that incorporate a single indenoindolyl ligand. First, an indenoindole or its synthetic equivalent is reacted with about one equivalent of a tetrakis(dialkylamino) Group 4 metal compound. The reaction product, a tris(dialkylamino) metal complex, is a versatile intermediate that can be halogenated, alkylated, or reacted directly with cyclopentadiene precursors to produce a variety of valuable indenoindolyl-Group 4 metal complexes. The process selectively provides mono-indenoindolyl complexes, enables the economical preparation of desirable Cp- or Cp-like derivatives, and permits the use of an inexpensive Group 4 transition metal source.

DETAILED DESCRIPTION OF THE INVENTION

Catalysts prepared by the process of the invention are "single site" in nature, i.e., they incorporate distinct chemical species rather than mixtures of different species. They give polyolefins with characteristically narrow molecular weight distributions (Mw/Mn<3) and good, uniform comonomer incorporation.

In each process of the invention, the initial step involves reaction of an indenoindole or its synthetic equivalent with about one equivalent of a tetrakis(dialkylamino) Group 4 metal compound. The reaction produces a tris(dialkylamino) indenoindolyl Group 4 metal complex, and it eliminates one equivalent of a dialkylamine or a dialkylamino-functional side product.

By "indenoindole," we mean an organic compound that has both indole and indene rings. The five-membered rings from each are fused, i.e., they share two carbon atoms. Preferably, the rings are fused such that the indole nitrogen and the only sp$^3$-hybridized carbon on the indenyl ring are "trans" to each other. Such is the case in an indeno[1,2-b] ring system such as:

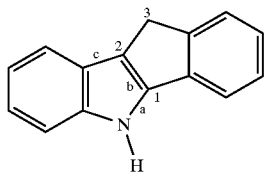

Suitable ring systems also include those in which the indole nitrogen and the sp$^3$-hybridized carbon of the indene are beta to each other, i.e., they are on the same side of the molecule. This is an indeno[2,1-b]indole ring system:

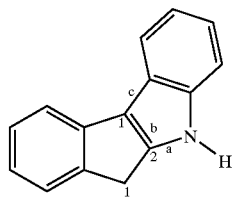

The ring atoms can be unsubstituted or substituted with one or more groups such as alkyl, aryl, aralkyl, halogen, silyl, nitro, dialkylamino, diarylamino, alkoxy, aryloxy, thioether, or the like. Additional fused rings can be present, as long as an indenoindole moiety is present.

Numbering of indenoindoles follows IUPAC Rule A-22. The molecule is oriented as shown below, and numbering is done clockwise beginning with the ring at the uppermost right of the structure in a manner effective to give the lowest possible number to the heteroatom. Thus, 5,10-dihydroindeno[1,2-b]indole is numbered as follows:

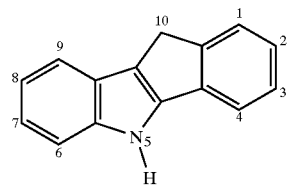

while 5,6-dihydroindeno[2,1-b]indole has the numbering:

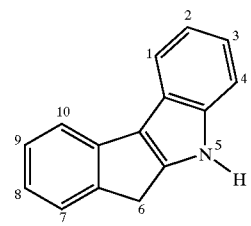

For correct nomenclature and numbering of these ring systems, see the *Ring Systems Handbook* (1998), a publication of Chemical Abstracts Service, Ring Systems File II: RF 33986-RF 66391 at RF 58952. (Note that indenoindoles are incorrectly numbered in U.S. Pat. No. 6,232,260; more correct numbering appears in PCT Int. Appl. WO 99/24446.)

Suitable indenoindoles useful in the process of the invention include, for example, 5,10-dihydroindeno[1,2-b]indole, 5,6-dihydroindeno[2,1-b]indole, 4,7-dimethyl-5,10-dihydroindeno[1,2-b]indole, 4-tert-butyl-8-methyl-5,10-dihydroindeno[1,2-b]indole, 4,8-dichloro-5,10-dihydroindeno-[1,2-b]indole, 2,7-dimethyl-5,6-dihydroindeno[2,1-b]indole, and the like.

Methods for making indenoindoles are well known. Suitable methods are disclosed, for example, in U.S. Pat. No. 6,232,260, the teachings of which are incorporated herein by reference, and references cited therein, including the method of Buu-Hoi and Xuong, *J. Chem. Soc.* (1952) 2225. Suitable procedures also appear in PCT Int. Appl. WO 99/24446.

A synthetic equivalent of an indenoindole can be used instead of an indenoindole. By "synthetic equivalent," we mean a compound that functions in the same way as an indenoindole when reacted with a tetrakis(dialkylamino) Group 4 metal compound. For a general discussion of synthetic equivalents, see F. A. Carey and R. J. Sundberg, *Advanced Organic Chemistry*, Part B (1977) pp. 418–419.

Suitable synthetic equivalents replace an acidic hydrogen from the indenyl 5-ring of an indenoindole compound with an organosilicon, organotin, or organogermanium group. Structures (a) and (b) below illustrate various synthetic equivalents of indenoindole compounds:

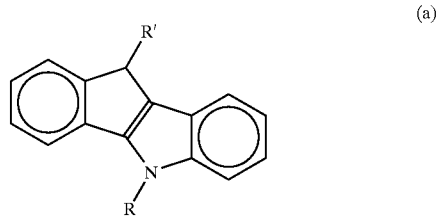

(a)

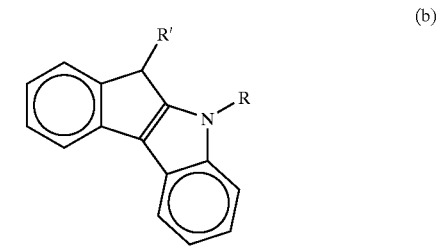

(b)

In the structures above, R is a hydrocarbyl group, preferably having from 1 to 30 carbons, and R' is selected from the group consisting of organotin, organosilicon, and organogermanium. Organosilicon groups, such as trimethylsilyl, are preferred.

When these synthetic equivalents are reacted with a tetrakis(dialkylamino) Group 4 metal compound, the desired tris(dialkylamino) indenoindolyl Group 4 metal complex is produced, along with an easily removed, dialkylamino-functional by-product, such as tri-n-butyl(N,N-dimethylamino)stannane or trimethyl(N,N-dimethylamino)silane. The reaction of the silyl-functional synthetic equivalent below with one equivalent of tetrakis(dimethylamino)zirconium is illustrative:

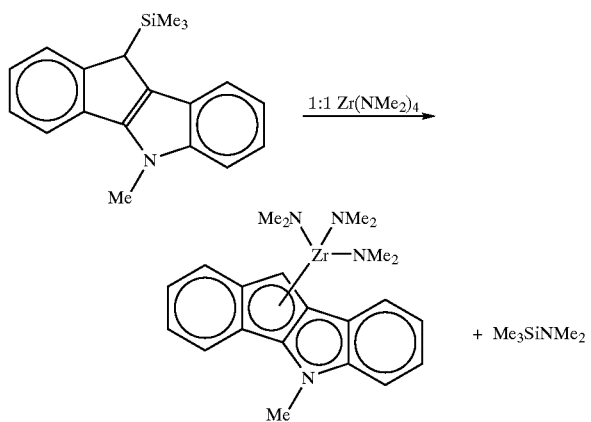

The synthetic equivalents can be made by numerous techniques that are well known to those skilled in the art. For example, a trimethylsilyl-substituted indenoindole is easily prepared by deprotonating an indenoindole with about one equivalent of n-butyllithium, and reacting the resulting monoanion with an equivalent of chlorotrimethylsilane. Similar strategies involving initial deprotonation and nucleophilic displacement can be used advantageously to attach organotin or organogermanium groups to the indene ring.

As noted above, a tetrakis(dialkylamino) Group 4 metal compound reacts with an indenoindole or its synthetic equivalent in the initial step of the process of the invention. Suitable tetrakis(dialkylamino) Group 4 metal compounds incorporate a Group 4 metal, i.e., zirconium, titanium, or hafnium, and four dialkylamino ligands, which may be the same or different. Preferably, the alkyl groups of the dialkylamino ligands have from 1 to 30 carbons, more preferably from 1 to 5 carbons. Suitable tetrakis(dialkylamino) Group 4 metal compounds include, for example, tetrakis(dimethylamino)zirconium, tetrakis(dimethylamino)titanium, tetrakis(dibutylamino)zirconium, tetrakis(N-methyl-N-ethylamino)-zirconium, bis(dimethylamino)bis(diethylamino)zirconium, and the like.

Methods for making the tetrakis(dialkylamino) Group 4 metal compounds are well known. In a preferred approach, they are made by reacting a Group 4 metal tetrahalide with at least about 4 equivalents of an alkali metal salt of a dialkylamine, such as lithium dimethylamide, usually in the presence of a dry organic solvent, preferably an aromatic hydrocarbon. The by-product, normally an alkali metal halide, precipitates and is separated by filtration. The organic solution, which contains the tetrakis(dialkylamino) Group 4 metal compound, can be evaporated to remove the organic solvent, or it can be used "as is" in the next reaction step. Some tetrakis(dialkylamino) Group 4 metal compounds can be purified by sublimation. A preferred method of preparing these compounds is described by Jordan et al. (*J. Am. Chem. Soc.* 118 at 8026).

Reacting the tetrakis(dialkylamino) Group 4 metal compound and the indenoindole or synthetic equivalent is straightforward. Usually, these components are simply dissolved or suspended in an organic solvent, preferably a hydrocarbon or halogenated hydrocarbon, and are heated to a temperature effective to promote amine elimination. Volatile amine side products can be removed by distillation or by stripping with vacuum, an inert gas purge, or both. Non-volatile by-products are removed by any suitable method, including, for example, extraction, filtration, decanting, or the like. Usually, non-volatile by-products are removed by filtration based on differential solubilities of the transition metal complex and by-products in the reaction solvent.

Preferably, the reaction is performed at a temperature within the range of about 30° C. to about 200° C., more preferably from about 60° C. to about 100° C.

The reaction product from the first step is a tris(dialkylamino) indenoindolyl Group 4 metal compound. This material, hereinafter sometimes called just "the intermediate," is valuable for making a variety of indenoindolyl Group 4 metal compounds. The intermediate can be isolated and purified. Usually, however, the crude intermediate is simply used "as is" in a subsequent reaction step. Preparation of an intermediate is exemplified below:

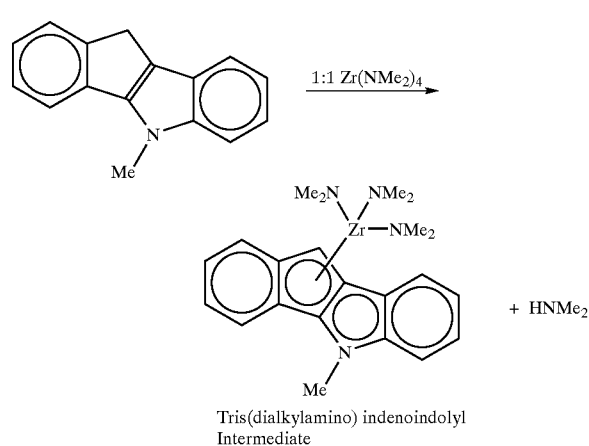

Tris(dialkylamino) indenoindolyl
Intermediate

In one aspect of the invention, the intermediate reacts with a halogenating agent to produce an indenoindolyl Group 4 metal trihalide. Suitable halogenating agents have the ability to cleave a dialkylamido nitrogen-Group 4 metal bond of the intermediate and replace the dialkylamino group with a halide. Examples include halide-containing acids, chlorine, bromine, iodine, silicon tetrahalides, organotin halides, N-halosuccinimides, organosilicon halides, and the like. A few other specific examples are hydrochloric acid, hydrobromic acid, chlorotrimethylsilane, tetrachlorosilane, tri-n-butyltin chloride, and N-bromosuccinimide. Halogenation is exemplifed by the reaction of the tris(dimethylamino) indenoindolyl zirconium complex shown below with chlorotrimethylsilane:

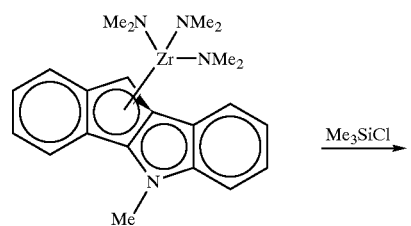

-continued

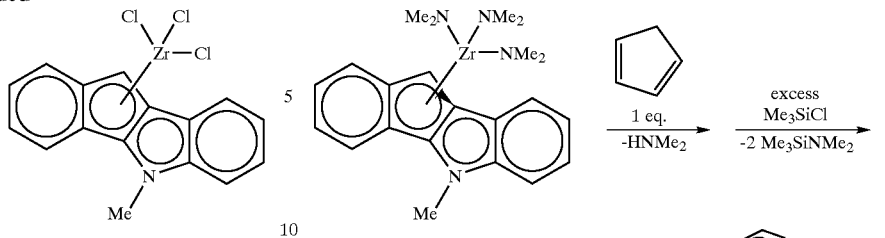

Often, halogenation involves little more than combining the reactants at room temperature, usually in an organic solvent, and separating a solution of the desired halogenated complex from insoluble by-products. See, for example, *J. Am. Chem. Soc.* 118 (1996) 8024 at 8030.

In another aspect of the invention, the tris(dialkylamino) indenoindolyl Group 4 metal intermediate reacts with an alkylating agent to produce an indenoindolyl Group 4 metal trialkyl. Suitable alkylating agents have the ability to cleave a dialkylamido nitrogen-Group 4 metal bond of the intermediate and replace the dialkylamino group with an alkyl group. Examples include alkylaluminums, alkylaluminum halides, Grignard reagents, dialkylmagnesium compounds, alkali metal alkyls, organoboranes, and the like. A few specific examples are triethylaluminum, di-n-butylmagnesium, methylmagnesium bromide, methyllithium, n-butyllithium, and tri-n-butylborane. One example:

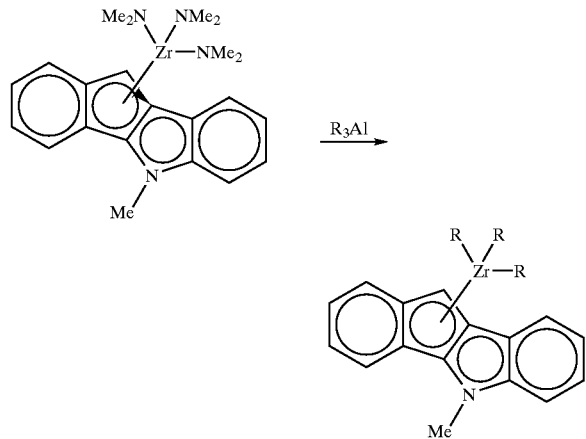

Alkylation is performed according to well-known methods. Again, the reaction usually involves only combination of the intermediate and the alkylating agent in an organic solvent, often at room temperature, followed by separation of the desired alkylated complex from insoluble by-products. See, for example, *J. Am. Chem. Soc.* 118 (1996) 8024 at 8030–8031.

The intermediate can also be reacted with cyclopentadiene or a Cp-like compound (indene, fluorene, etc.) to produce a bis(dialkylamino) indenoindolyl Group 4 metal compound that incorporates a cyclopentadienyl or Cp-like ligand. This reaction product can be subsequently halogenated or alkylated as described in the preceding paragraphs. For example:

The initial reaction step normally involves heating the intermediate and the cyclopentadiene compound, optionally in the presence of an organic solvent, and stripping out a gaseous dialkylamine by-product. See, for example, *J. Am. Chem. Soc.* 118 (1996) 8024 at 8031.

Catalysts produced by the process of the invention are optionally used with an activator. Suitable activators help to ionize the organometallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis(pentafluorophenyl)aluminate, anilinium tetrakis-pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Suitable activators also include aluminoboronates--reaction products of alkyl aluminum compounds and organoboronic acids--as described in U.S. Pat. Nos. 5,414,180 and 5,648,440, the teachings of which are incorporated herein by reference.

Catalysts prepared by the process of the invention are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or—boron compounds. See, for example, the techniques described in U.S. Pat. No. 6,211,311, the teachings of which are incorporated herein by reference.

The catalysts are useful for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psig to about 50,000 psig. More preferred is the range from about 15 psig to about 1000 psig.

The following examples merely illustrate the invention. Those skilled in the art will recognize many variations that are within the spirit of the invention and scope of the claims.

EXAMPLE 1

Preparation of a Tris(dimethylamino)zirconium Intermediate

A 500-mL flask equipped with a stir bar is charged with tetrakis(dimethylamino)zirconium (7.92 g, 29.6 mmol) and 5,8-dimethyl-5,10-dihydroindeno[1,2-b]indole (6.90 g, 29.6 mmol). Toluene (240 mL) is added at room temperature to afford an orange solution. The mixture is heated to 100° C. under a nitrogen purge (open to a bubbler) with stirring for 48 h. The yield of (5,8-dimethyl-5,10-dihydroindeno[1, 2-b] indolyl)-tris(dimethylamino)zirconium, as measured by $^1$H NMR spectroscopy versus unconsumed starting material, is 59.2 mol %.

EXAMPLE 2

Halogenation of the Intermediate

A portion of the product from Example 1 (0.10 g, 0.23 mmol) and toluene (50 mL) are combined and stirred in a flask at room temperature. Neat trimethylsilyl chloride (0.30 mL, 2.3 mmol) is added by syringe under a nitrogen purge. The reaction is complete within minutes, and the product is isolated by filtration. The expected product is (5,8-dimethyl-5,10-dihydroindeno[1,2-b]indolyl)zirconium trichloride.

EXAMPLE 3

Preparation of a Cyclopentadienyl Dichloride Complex

The trihalide product from Example 2 is suspended in diethyl ether (50 mL) under nitrogen and cooled to −78° C. A solution of cyclopentadienyl sodium (2.0 M solution in tetrahydrofuran, 1.05 eq., 0.12 mL) is added by syringe, and the mixture is allowed to warm to room temperature overnight. The mixture is filtered, and the solids are washed with hexane and dried. The expected product is cyclopentadienyl (5,8-dimethyl-5,10-dihydroindeno[1,2-b]indolyl)zirconium dichloride.

EXAMPLE 4

Grignard Alkylation of the Intermediate

A portion of the product from Example 1 (0.10 g, 0.23 mmol) is dissolved in diethyl ether (50 mL) at room temperature, and methylmagnesium bromide (3.0 M solution in diethyl ether, 3.0 eq., 0.23 mL, 0.69 mmol) is added by syringe. The mixture is stirred overnight, and 1,4-dioxane (6.0 eq., 120 mg, 0.12 mL) is added to precipitate the magnesium salts. The mixture is filtered and volatiles are removed to give the desired alkylated product. The expected product is (5,8-dimethyl-5,10-dihydroindeno[1,2-b]indolyl) zirconium trimethyl.

EXAMPLE 5

Preparation of a Cyclopentadienyl Bis (dialkylamine) Complex

A portion of the product from Example 1 (0.10 g, 0.23 mmol) is dissolved in toluene (50 mL), and freshly cracked cyclopentadiene (0.066 g, 1.0 mmol) is added. The solution is heated at reflux for 16 h. The volatiles are removed under vacuum and the crude solids are recrystallized from toluene. The expected product is cyclopentadienyl(5,8-dimethyl-5, 10-dihydroindeno[1, 2-b1indolyl)bis-(dimethylamino) zirconium.

EXAMPLE 6

Preparation of a Cyclopentadienyl Dichloride Complex

The product from Example 5 (about 0.23 mmol) is suspended in diethyl ether (50 mL) and cooled to 0C. Hydrochloric acid (1.0 M solution in diethyl ether, 2.0 eq., 0.46 mL) is added under nitrogen. The resulting precipitate is washed with hexanes. The expected product is cyclopentadienyl(5,8-dimethyl-5,10-dihydroindeno[1,2-b] indolyl)zirconium dichloride.

COMPARATIVE EXAMPLE 7

Attempted Preparation of Mono-Indenoindolyl Complex from $ZrCl_4$

A flask with stir bar is charged with zirconium tetrachloride (1.37 g, 5.90 mmol) and toluene (20 mL). Diethyl ether (20 mL) is added, and the mixture is stirred at room temperature. A suspension of 5,8-dimethyl-5,10-dihydroindeno[1,2-b]indolyllithium (1.41 g, 5.90 mmol) in toluene (10 mL) is combined with diethyl ether (4 mL) to give an orange solution. This orange solution is added dropwise to the zirconium tetrachloride solution with stirring at room temperature. The mixture turns deep red and a precipitate forms. Stirring continues at room temperature for 48 h. The mixture is filtered and washed with toluene (30 mL) followed by hexanes (30 mL), and the solid is dried under vacuum. Analysis by $^1$H NMR spectroscopy reveals that bis(5,8-dimethyl-5,10-dihydroindeno[1, 2-b]indolyl) zirconium dichloride is the only product.

The preceding examples are meant only as illustrations. The following claims define the invention.

I claim:
1. A process which comprises:
  (a) reacting an indenoindole or its synthetic equivalent with about one equivalent of a tetrakis(dialkylamino) Group 4 metal compound; and
  (b) reacting the product from step (a) with an excess of a halogenating agent to produce an indenoindolyl Group 4 metal trihalide.
2. The process of claim 1 wherein the indenoindolyl Group 4 metal trihalide is further reacted with about one equivalent of a cyclopentadienyl anion to produce a cyclopentadienyl(indenoindolyl) Group 4 metal dihalide.

3. A process which comprises:
(a) reacting an indenoindole or its synthetic equivalent, with about one equivalent of a tetrakis(dialkylamino) Group 4 metal compound; and
(b) reacting the product from step (a) with an excess of an alkylating agent to produce an indenoindolyl Group 4 metal trialkyl.

4. A process which comprises:
(a) reacting an indenoindole or its synthetic equivalent, with about one equivalent of a tetrakis(dialkylamino) Group 4 metal compound; and
(b) reacting the product from step (a) with about one equivalent of a cyclopentadiene compound to produce a cyclopentadienyl (indenoindolyl) Group 4 metal bis (dialkylamino) compound.

5. The process of claim 4 wherein the product from step (b) is further reacted with an excess of a halogenating agent to produce a cyclopentadienyl (indenoindolyl) Group 4 metal dihalide.

6. The process of claim 4 wherein the product from step (b) is further reacted with an excess of an alkylating agent to produce a cyclopentadienyl (indenoindolyl) Group 4 metal dialkyl.

* * * * *